United States Patent [19]
Grandi et al.

[11] Patent Number: 5,674,712
[45] Date of Patent: Oct. 7, 1997

[54] **RECOMBINANT VECTOR AND USE THEREOF FOR EXOCELLULAR PREPARATION OF ANTIBODIES IN SINGLE MOLECULE FORM FROM *BACILLUS SUBTILIS***

[75] Inventors: Guido Grandi, Segrate; Francesca De Ferra, Lodi; Claudio Tosi, Busto Arsizio; Ornella Tortora, Milan; Anna Cuzzoni, Pavia, all of Italy

[73] Assignee: Eniricerche S.p.A., Milan, Italy

[21] Appl. No.: 207,169

[22] Filed: Mar. 8, 1994

[30] Foreign Application Priority Data

Mar. 10, 1993 [IT] Italy ................... MI93A0456

[51] Int. Cl.$^6$ ................ C12P 21/08; C12N 15/63; C12N 15/13; C12N 15/75
[52] U.S. Cl. .............. 435/69.6; 435/71.2; 435/172.3; 435/252.31; 435/252.5; 435/320.1; 435/839; 536/23.53; 536/23.1; 536/23.7; 536/24.1; 530/387.3; 530/867; 530/388.24; 530/808; 935/22; 935/29; 935/48; 935/74
[58] Field of Search ................ 435/172.3, 69.6, 435/71.2, 252.31, 252.5, 320.1, 839; 536/23.53, 23.1, 23.7, 24.1; 530/387.3, 867, 388.24, 808; 935/22, 29, 48, 74

[56] References Cited

FOREIGN PATENT DOCUMENTS

| 0 306 673 | 3/1989 | European Pat. Off. . |
| 0 321 940 | 6/1989 | European Pat. Off. . |
| 0 409 098 | 1/1991 | European Pat. Off. . |
| 88/10270 | 12/1988 | WIPO . |

OTHER PUBLICATIONS

Critical Reviews in Biotechnology, vol. 12, Issues 5,6, 1992, pp. 437–462, J.S. Sandhu, "Protein Engineering of Antibodies".

*Primary Examiner*—Ronald B. Schwadron
*Attorney, Agent, or Firm*—Oblon, Spivak, McClelland, Maier & Neustadt, P.C.

[57] ABSTRACT

A recombinant vector for the expression and secretion of antibodies in single molecule form (scFv) from *B. subtilis*, where said vector comprises the promoter of the gene for neutral protease, a new secretion sequence (I) and a DNA sequence coding a scFv antibody of interest, a strain of *B. subtilis* transformed with said recombinant vector, and a process for the exocellular production of scFv antibodies by culturing said strain of *B. subtilis* are described. The recombinant vector allows the expression of scFv in a completely soluble form and its secretion in high yields.

12 Claims, 3 Drawing Sheets

Fig.1

| | |
|---|---:|
| CAG GTC CAA CTG CAG CAG TCG GGG GCA GAG CTT ATG | 36 |
| Gln Val Gln Leu Gln Gln Ser Gly Ala Glu Leu Met | |
| AAG CCA GGG GCC TCA GTC AAG TTG ACA GCT TCC TGC | 72 |
| Lys Pro Gly Ala Ser Val Lys Leu Thr Ala Ser Cys | |
| TCT GGC TTC AGC ATT AAA GAC ACC TAT ATG CAC TGG | 108 |
| Ser Gly Phe Ser Ile Lys Asp Thr Tyr Met His Trp | |
| GTG AAG CAG AGG CCT GAA CAG GGC CTG GAG TGG ATT | 144 |
| Val Lys Gln Arg Pro Glu Gln Gly Leu Glu Trp Ile | |
| GGA AGA ATT GAT CCT GCG AAT GGT AAT ACT AAA TAT | 180 |
| Gly Arg Ile Asp Pro Ala Asn Gly Asn Thr Lys Tyr | |
| GAC CCG AAG TTC CAG GGC AAG GCC ACT ATA ACA GCA | 216 |
| Asp Pro Lys Phe Gln Gly Lys Ala Thr Ile Thr Ala | |
| GAC ACA TCC TCC AAC ACA GCC TAC CTG CAG CTC AGC | 252 |
| Asp Thr Ser Ser Asn Thr Ala Tyr Leu Gln Leu Ser | |
| AGC CTG ACA TCT GAG GAC ACT GCC GTC TAT TAC TGC | 288 |
| Ser Leu Thr Ser Glu Asp Thr Ala Val Tyr Tyr Cys | |
| CAT AGG TTC GAA TTT GCT ATG GAC TAC TGG GGC CAA | 324 |
| His Arg Phe Glu Phe Ala Met Asp Tyr Trp Gly Gln | |
| GGG ACC ACG GTC ACC | 339 |
| Gly Thr Thr Val Thr | |

Fig. 2

| | |
|---|---:|
| GAC ATT CAA GGT ACC CAG TCT CCA GCT TCC TTA GTT | 36 |
| Asp Ile Gln Gly Thr Gln Ser Pro Ala Ser Leu Val | |
| GTA TCT CTG GGG CAG AGG GCC ACC ATC TCA TGC AGG | 72 |
| Val Ser Leu Gly Gln Arg Ala Thr Ile Ser Cys Arg | |
| GCC AGC AAA AGT GTC AGT GCA TCT GGC TAT AGT TAT | 108 |
| Ala Ser Lys Ser Val Ser Ala Ser Gly Tyr Ser Tyr | |
| GTG AAT TGG TAT CAA CAG AAA CCA GGA CAG CCA CCC | 144 |
| Val Asn Trp Tyr Gln Gln Lys Pro Gly Gln Pro Pro | |
| AAA CTC CTC ATC TAT CTT GCA TCC AAC CTA GAA TCT | 180 |
| Lys Leu Leu Ile Tyr Leu Ala Ser Asn Leu Glu Ser | |
| GGG GTC CCT GCC AGG TTC AGT GGC AGT GGG TCT GGG | 216 |
| Gly Val Pro Ala Arg Phe Ser Gly Ser Gly Ser Gly | |
| ACA GAC TTC ACC CTC AAC ATC CAT CCT GTG GAG GAG | 252 |
| Thr Asp Phe Thr Leu Asn Ile His Pro Val Glu Glu | |
| GAG GAT GCT GCA ACT TAT TAC TGT CAG CAC AGT AGG | 288 |
| Glu Asp Ala Ala Thr Tyr Tyr Cys Gln His Ser Arg | |
| GAG CTT CCG CTC ACG TTC GGT GCT GGG ACC AAG CTG | 324 |
| Glu Leu Pro Leu Thr Phe Gly Ala Gly Thr Lys Leu | |
| GAG ATC TCC | 333 |
| Glu Ile Ser | |

5,674,712

RECOMBINANT VECTOR AND USE THEREOF FOR EXOCELLULAR PREPARATION OF ANTIBODIES IN SINGLE MOLECULE FORM FROM *BACILLUS SUBTILIS*

This invention relates in general to the exocellular production of antibodies in single molecule form (scFv) from *Bacillus subtilis* (*B.subtilis*).

In particular, this invention relates to a recombinant vector which comprises the promoter of the gene for neutral protease, a new secretion sequence and a DNA sequence coding a scFv antibody of interest, a strain of *B.subtilis* transformed with said recombinant vector and a process for the exocellular production of scFv antibodies by culturing of said strain of *B.subtilis*.

The possibility of obtaining antibody fragments (mini-antibodies) by their expression in bacterial cells has opened up new and interesting application prospects.

In fact, their reduced dimensions allow an improvement in pharmacokinetic characteristics for diagnostic and therapeutic uses. In addition, the production of mini-antibodies in microorganisms is economically more favourable than the production of monoclonal antibodies (mAbs) in mammalian cells since greater reproducibility of the preparations and a complete absence of possible contaminants from oncogenic viral DNA are guaranteed. The antibodies are tetrameric proteins formed from two heavy chains (H) and two light chains (K or lambda). In the H chain a variable region (VH) and three constant regions may be observed, while in the light chain only one constant region is present in addition to the variable region (VK). The variable parts, which are at the amino-terminal end of each chain, are responsible for binding to the antigen whereas the constant portions interact with the other components of the immune system (effector function). The regions responsible for binding to the antigen and those with an effector function may be separated by enzymatic digestion without altering their functionality. Indeed, it is known that the Fv portion of the antibody, ie VH+VK, isolated by means of enzymatic digestion of IgG, maintains totally its ability to bind to the antigen.

The use of said portion of the antibody, which forms the entire antigen-binding site, may present some stability problems for the Fv in that the two chains, not being covalently bound, tend to dissociate.

Recently some strategies have been proposed to reduce the drawback of the two chains dissociating.

Of particular interest appears to be that described by Bird et al., 1988 (Science, 242:423–426) which consists of the expression in *E.coli* of a molecule formed by the union of the variable regions of the two chains by way of a suitable peptide (linker). The two regions VH and VK are thus synthesized into a single molecule (scFv), with the carboxyl end of the VK region bound to the amino-terminal end of the VH, or vice-versa, by means of the linker.

When using this strategy, however, Bird et al. obtained an expression of scFv inside the cell in the form of non-functional insoluble aggregates. The functionality of these molecules may be recovered only by following complex procedures which, though efficient (Bird et al. report renaturing yields of 5% to 30%), are of no advantage when compared with systems where antibodies are produced in a soluble and functional form.

The known art describes systems for the secretion of functional scFv in the periplasm of *E coli*, an environment from which antibody molecules may be recovered following controlled lysis of the bacteria.

Currently particular attention is being given to the development of systems for the synthesis and secretion of recombinant molecules in *B.subtilis*.

*B.subtilis* is in fact an interesting microorganism from the biotechnological viewpoint: It is completely non-pathogenic, has the ability to secrete the product of gene expression into culture medium and is easy to cultivate on a large scale.

A partial limitation on the use of this microorganism is the lack of vectors which allow an efficient exocellular production of scFv antibodies. Bird et al. (U.S. Pat. No. 4,946,778) obtained 1 mg/liter of scFv using systems of expression and secretion in *B.subtilis* comprising the promoter regions and secretion sequence isolated from the genes coding for proteolytic enzymes.

Recently a new system for improving secretion of scFv in *B.subtilis* (Wu et al., 1993, Biotechnology, 11:71–76) was proposed. The values obtained (5 mg/liter), however, still appeared to be of little interest for industrial use. It has been found that the disadvantages of the above mentioned technology may now be overcome by adopting a particular recombinant vector which comprises the promoter of the gene for neutral protease and a DNA sequence coding for a new secretion peptide.

In particular, said recombinant vector allows the expression in *B.subtilis* of scFv antibodies in a completely soluble form and their secretion in high yields.

An object of the present invention is a recombinant vector for the expression and secretion of antibodies from single molecule form in *B.subtilis* which comprises the promoter of the gene for neutral protease, a new secretion sequence and a DNA sequence coding for an antibody in single molecule form.

A further object of the present invention is a strain of *B.subtilis* transformed with said recombinant vector.

A further object of the present invention is a process for the exocellular preparation of said antibodies which comprises the cultivation of a strain of *B.subtilis* transformed with said recombinant vector and the removal from the culture medium of antibodies in single molecule form.

A further object of the present invention is the use of said antibodies in diagnostics and therapy.

A further object of the present invention is the DNA sequence coding for a new secretion peptide signal.

A further object of the present invention is the antibody scFv5E8 specific for sub-unit alpha of human chorionic gonadotropin.

Further objects of the present invention will be apparent from the description and examples which follow.

DESCRIPTION OF THE FIGURES

FIG. 1: this shows the nucleotide (SEQ ID NO:1) and amino acid (SEQ ID NO:2) sequence of the variable region of the heavy chain (VH) of the monoclonal antibody 5E8 specific for sub-unit alpha of human gonadotropin.

FIG. 2: this shows the nucleotide (SEQ ID NO:3) and amino acid (SEQ ID NO:4) sequence of the variable region of the light chain (VK) of the monoclonal antibody 5E8 specific for sub-unit alpha of human gonadotropin.

DETAILED DESCRIPTION OF THE INVENTION

Figure 3:
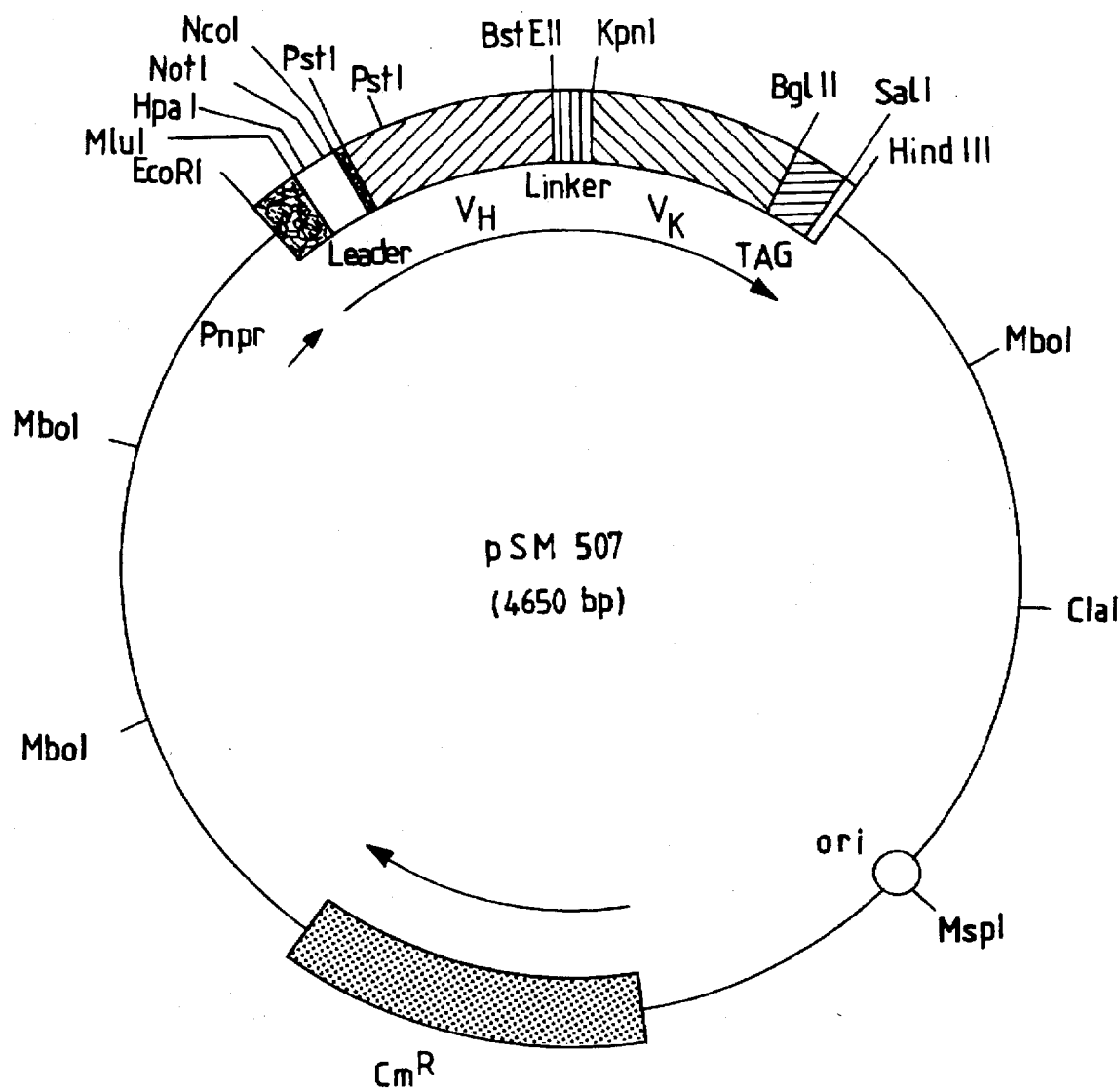
FIG. 3: this shows the restriction map of the recombinant vector pSM507.

In particular, the recombinant vector of the present invention comprises:

1) the promoter of the gene for neutral protease of B.subtilis BGSC 1A341;

2) the secretion sequence (I) (SEQ ID NO:5) 5' ATG AGA AGC AAA AAA ACG CGT ATC AGC TTG TTG TTT GCG TTA ACG TTA ATC TTT ACG ATG GCA TTC AGC GGC CGC TCT GCC ATG GCC 3' and 3) a DNA sequence coding for an antibody in single molecule form with the sequence VH/VK-L-VK/VH-(TAG)$_n$
where:

VH and VK are the variable regions of the heavy and light chains of an antibody of interest; L (Linker) is the peptide linker between the two variable regions Val-Ser-Ser-(Gly$_4$-Ser)$_3$ (SEQ ID NO:7); TAG is a peptide recognised by polyclonal antibodies directed towards the same peptide, n is 1 or 0.

The secretion sequence (I) (SEQ ID NO:5), or sequence leader (LS), codes for a new secretion peptide with the following amino acid sequence (SEQ ID NO:6):

Met Arg Ser Lys Lys Thr Arg Ile Ser Leu Leu Phe Ala Leu Thr Leu Ile Phe Thr Met Ala Phe Ser Gly Arg Ser Ala Met Ala.

The recombinant vector of the present invention may be obtained by:

a) synthesis of an oligonucleotide which comprises the secretion sequence (I), the sequence coding for the peptide linker and optionally the sequence coding for the peptide TAG and wherein said oligonucleotide contains unique restriction sites which allow the insertion of the sequence coding for the variable region of the heavy or light chain of the antibody downstream of secretion sequence (I) and upstream of the peptide linker and the insertion of the sequence coding for the variable region of the light or heavy chain of the antibody downstream of the peptide linker and upstream of the peptide TAG;

b) cloning of said oligonucleotide in a plasmid vector comprising the promoter of the gene for of B.subtilis BGSC 1A341 neutral protease;

c) cloning of the DNA sequences coding for the variable region of the heavy and light chains of the antibody of interest in the oligonucleotide restriction sites; and finally d) isolation of the recombinant vector.

According to one embodiment of the present invention the oligonucleotide in step a) has the sequence (L1) (SEQ ID NO:8):

| EcoRI | |
|---|---|
| 5'GAA TTC TTA TGA GAA GCA AAA AAA CGC GTA | 30 |
| TCA GCT TGT TGT TTG CGT TAA CGT TAA TCT TTA | 63 |
| CGA TGG CAT TCA GCG GCC GCT CTG CCA TGG CCG | 96 |
|         Psti     BstEII | |
| CAC AGG TCC AAC TGC AGC CTA TGG TCA CCG TCT | 129 |
| CCT CAG GTG GCG GTG GCT CTG GCG GTG GTG GGT | 162 |
|         KpnI | |
| CGG GTG GCG GCG GAT CTG ACA TTC AAG GTA CCC | 195 |
| BGlII | |
| CCT GAG ATC TCA TGG AAG AAC TTA TGA TCG AGG | 228 |
|      SalI   HindIII | |
| GTA GGT AAG TCG ACA AGC TT 3' | 248 |
| Stop | | wherein immediately downstream from the secretion sequence (I) (from nucleotides 9 to 95 inclusive) there are 4 restriction sites (PstI, BstEII, KpnI and BglII) positioned in such a way as to be able to clone in the same reading frame the DNA sequences coding for the variable region of the heavy chain (VH) and the light chain (VK) respectively. Between the BstEII site (C-terminal region of the V$_H$) and the KpnI site (N-terminal region of V$_K$), the sequence codes for a peptide linker between the two regions, having the sequence Val-Ser-Ser-(Gly$_4$-Ser)$_3$; furthermore, the sequence which follows the BglII site codes for a nonapeptide with the sequence Met-Glu-Glu-Leu-Met-Ile-Glu-Gly-Arg useful as a specific target of recognition by anti-peptide antibodies for monitoring the expression of the protein, using the Western blot method, and for its purification. This sequence is followed by a stop codon for translation and the restriction sites SalI and HindIII.

In the preferred embodiment, the plasmid vector in step b) is pSM308 ATCC 68047 comprising the origin of replication in B.subtilis, the gene CAT coding for chloramphenicol resistance, the promoter for neutral protease (npr) of the strain B.subtilis BGCS 1A341, an EcoRI restriction site located immediately downstream of the promoter and the ribosomal recognition site (RBS) and a HindIII site upstream from the EcoRI site. The plasmid pSM308 was deposited with the American Type Culture Collection, 12301 Parklawn Drive, Rockville Md. 20852 under accession number ATCC 68047 on Jul. 13, 1989.

The cloning of the oligonucleotide may be conducted according to normal techniques, using a plasmid vector previously digested with suitable restriction enzymes. Subsequently, from positive clones obtained by techniques of transformation and selection, cloning plasmids useful for the construction of the recombinant vector may be isolated.

By operating in preferred conditions, a plasmid vector of about 4 Kb is obtained, denominated pSMA, in which L1 is correctly inserted downstream from the promoter npr.

The introduction of the sequences coding for the variable regions of the heavy and light chains of an antibody in the restriction sites of the oligonucleotide L1 results in the construction of the recombinant vector which, according to the present invention, starting from a single promoter, allows the simultaneous expression in the same cell of a completely soluble precursor having the following sequence:

LS-VH-L-VK-TAG where:

LS is the DNA sequence (I) (SEQ ID NO:5) coding for the new secretion peptide signal;

VH is the variable region of the heavy chain;

VK is the variable region of the light chain;

L is the peptide linker Val-Ser-Ser-(Gly$_4$-Ser)$_3$ (SEQ ID NO:7) and

TAG is the nonapeptide Met-Glu-Glu-Leu-Met-Ile-Glu-Gly-Arg (SEQ ID NO:10).

Said precursor is then processed correctly at membrane level and the antibody VH-L-VK-TAG is secreted in the culture medium at a high yield.

The sequences coding for the variable regions VH and VK may be selected from those of monoclonal antibodies specific to an antigen of interest.

By way of non-limiting example of the invention, the coding sequences (genes) for the variable regions of the heavy and light chains of the monoclonal antibody 5E8 specific for sub-unit alpha of human chorionic gonadotropin were cloned (A. Albertini et al., 1987 ("Human Tumor Markers", Ed. Walter de Gruyter & Co., Berlin) 387–401).

From a hybridoma culture producing monoclonal antibodies 5E8, all mRNA was extracted from which was subsequently amplified the DNA coding for the variable regions of the light (VK5E8) and heavy chains (VH5E8) of the antibody in question. The operations were conducted following the usual methods employing two pairs of oligonucleotides as primers, which hybridize at the 5' and 3' ends respectively of the genes coding for said regions.

By means of the amplification technique DNA fragments were obtained which comprised the gone VH5E8 delimited at the 5' end by a PstI site and at the 3' end by a BstEII site and the gene VK5E8 delimited at the 5' end by a KpnI site and at the 3' by a BglII site.

The DNA fragments digested with the pair of restriction enzymes PstI and BstEII, and KpnI and BglII were cloned in the vector pSMA obtaining the recombinant vector psM507.

In accordance with the present invention, recombinant vectors characterised by combinations of promoters/secretion sequences different from npr/(LSI) were constructed.

For this purpose the plasmid pSM268 was used, comprising a constitutive promoter (Pc), the origin of replication in B.subtilis, the gene coding for resistance to chloramphenicol and the restriction sites EcoRI, situated immediately downstream IROM the binding consensus sequence for the ribosomes (RBS) for B.subtilis, and HindIII located downstream of the EcoRI site.

Said plasmid was obtained from pSM214 ATCC 67320 by deletion of the region AvaII-XbaI (which comprises the origin of replication in E.coli and the sequence Km$^r$) and subsequent circularisation with T4 DNA ligase.

An oligonucleotide (L2) was then synthesized, comprising the sequence of 22 triplets coding for the leader peptide of the gene pelB of Erwinia carotovora (Lei, S. P. et al., 1987, J. Bacteriol. 169, 4379) and having the following sequence (SEQ ID NO:11):

| EcoRI | |
|---|---|
| 5' GAA TTC ATA TGA AAT ACC TAT TGC CTA CGG | 30 |
| CCG CCG CTG GAT TGT TAT TAC TCG CTG CCC AAC | 63 |
| PstI | |
| CAG CCA TGG CCG CAC AGG TCC AAC TGC AGC CTA | 96 |
| BstEII | |
| TGG TCA CCG TCT CCT CAG GTG GCG GTG GCT CTG | 129 |
| GCG GTG GTG GGT CGG GTG GCG GCG GAT CTG ACA | 162 |
| KpnI    BglII | |
| TTC AAG GTA CCC CCT GAG ATC TCA TGG AAG AAC | 195 |
| SAlI  HindIII | |
| TTA TGA TCG AGG GTA GGT AAG TCG ACA AGC TT 3' | 227 |
| Stop | |

Finally, the construction of the following cloning plasmids was undertaken:
  pSMB comprising the npr promoter and the oligonucleotide L2 (SEQ ID NO:11) (secretion sequence signal of pelB);
  pSMC comprising the constitutive promoter Pc and the oligonucleotide L1 (SEQ ID NO:8) (secretion sequence signal I) and
  pSMD comprising the constitutive promoter Pc and the oligonucleotide L2 (SEQ ID NO:11) (secretion sequence signal of pelB).

The cloning in said plasmids of DNA fragments comprising the gene VH5E8 and the gene VK5E8 has led to the isolation of the recombinant vectors pSM438 (npr/pelB), pSM443 (Pc/sequence (I)) and pSM442 (Pc/pelB).

Subsequently, cells of B.subtilis transformed with said vectors were cultivated in a suitable culture medium. From analysis of the intracellular and exocellular proteins of said culture it was shown that:

the plasmid pSM507 gives rise to the accumulation of at least 30 mg/liter of soluble antibody in the supernatant;

the plasmid psM442 is responsible for the expression of high levels of antibody (10% of total proteins) but almost exclusively of intracellular and insoluble form;

the plasmid psM438 results in the secretion of scFv at a quantity three times less than plasmid pSM507 and gives rise to the accumulation of precursor in an insoluble form, and finally the plasmid psM443 does not give rise to accumulation of precursor but to a level of secretion lower than that found with plasmid psM507.

These results indicate that the combination of promoter of the gene for neutral protease/secretion sequence signal (I) is fundamental for optimum expression and secretion of the antibody.

Therefore, the recombinant vector according to the present invention is useful for the exocellular production of scFv antibodies by a fermentation process which uses a strain of B. subtilis transformed with said vector.

Typically the process may be carried out by cultivating a strain of B.subtilis transformed with the recombinant vector of the present invention in a culture medium containing a source of carbon, a source of nitrogen and microelements, then isolating the antibody scFv secreted therein.

Said antibodies may be purified by one of the techniques normally used in this particular field of work.

Binding and affinity tests carried out on the crude cellular extract obtained from the culture medium of B.subtilis cells (pSM507) indicate that interaction characteristics at the binding site of scFv5E8 compared with the monoclonal antibody of origin are maintained.

Therefore the antibody in single molecule form, a further object of the present invention, may be used in diagnostics for the determination of endocrine tumours and, in general, tumours of trophoblastic origin.

The plasmid pSM507 was deposited with the American Type Culture Collection, 12301 Parklawn Drive, Rockville, Md. 20852 under accession number ATCC 69173 on Jan. 14, 1993.

The following examples have the purpose of illustrating the present invention without limiting its scope.

EXAMPLE 1

Construction of Cloning Vector pSMA

The plasmid pSM308 ATCC 68047 (10 µg) was digested with the enzymes EcoRI and HindIII (Boehringer) at 37° C. for 1 hour.

The reaction was immediately blocked with EDTA 20 mM (final concentration).

An aliquot of the digestion mixture was ligated with the oligonucleotide L1, synthesized by means of the System Plus (Beckman) automatic synthesizer, in a ligase mixture (1 mM ATP, 20 mM Tris-HCl pH 7.6, 10 mM MgCl$_2$ and 10 mM DTT) containing 2 U of T4 DNA ligase. The reaction was conducted at 14° C. for one night. Finally the ligase mixture was used to transform cells of B.subtilis SMS330 (rec$^+$, npr$^-$, apr$^-$) rendered competent according to the method described by Contente and Dubnau (Mol. Gen. Genet. 167, 251–258, 1979).

The recombinant clones were selected onto plates of TBAB (DIFCO) containing 5 µ/ml of chloramphenicol (Cm). From a positive clone (Cm$^R$) the plasmid vector named pSMA was isolated.

EXAMPLE 2

Construction of the Cloning Vectors pSMB, pSMC and pSMD

The plasmids pSM308 ATCC 68047 and pSM268 (10 µg) were digested with the restriction enzymes EcoRI and HindIII and then ligated separately with the oligonucleotide L1 or the oligonucleotide L2. The ligase mixtures were then used to transform suitable cells of *B.subtilis* SMS330. Finally, from the positive clones selected onto medium containing Cm, the following cloning vectors were isolated:

pSMB comprising the promoter npr and the oligonucleotide L2 (secretion sequence signal of pe1B)

pSMC comprising the constitutive promoter Pc and the oligonucleotide L1 (secretion sequence signal (I)) and pSMD comprising the constitutive promoter Pc and the oligonucleotide L2 (secretion sequence signal of pe1B).

EXAMPLE 3

Cloning of the Variable Regions of the Heavy and Light Chains of MAb5E8 Specific for Sub-unit Alpha of Human Gonadotropin The following primers were utilised for the cloning:

1) VH₁FOR having the sequence: (SEQ ID NO:13)

BstEII

5'TGAGGAGACG GTGACCCTGG TCCCTTGGCC CCAG 3' used for annealing to the 3' end of the strand of the sequence coding for the variable region of the heavy chain;

2) VK₁FOR having the sequence (SEQ ID NO:14):

BglII

5'GTTAGATCTC CAGCTTGGTC CC 3' used for annealing to the 3' terminal of the helix of the sequence coding for the variable region of the light chain;

3) VH1BACK having the sequence (SEQ ID NO:15):

PstI

5'AGGTIIAICT GCAG(G/C)AGTCI GG 3' used for annealing to the 3' end of the antisense strand of the sequence coding for the variable region of the heavy chain;

4) VKBACK having the sequence (SEQ ID NO:16):

KpnI

5'GACATTCAGG GTACCCAGTC TCCA 3' used for annealing to the 3' end of the antisense strand of the sequence coding for the variable region of the light chain.

A) Preparation of cDNA

The hybridoma which produces the monoclonal antibodies 5E8 specific for sub-unit alpha of human gonadotropin was cultivated in the medium RPMI 1640 supplemented with foetal bovine serum at 10%, L-glutamine 200 mM, penicillin and streptomycin and about 4×10⁷ cells were used to isolate all the RNA. The mRNA polyA⁺ was separated from the total RNA by an extraction technique using guanidine-isothiocyanate (RNA extraction kit supplied by Stratagene) followed by affinity chromatography on oligodT cellulose (Boehringer).

With the object of cloning the sequence coding for the variable region of the heavy chain, 25 µl of a reaction solution containing 5 µg of mRNA, 20 pmoles of the primer VH₁FOR, 250 µM of each of dATP, dTTP, dCTP and dGTP, 10 mM of dithiotreitol (DTT), 100 mM of Tris-HCl, 10 mM of MgCl₂ and 140 mM of KCl, pH 8.3 were prepared. The reaction solution was heated to 65° C. for 10 minutes and then cooled to room temperature to allow annealing of the primer to the 3' end of the sequence coding for the variable region of mRNA.

After adding 2 µl of mouse Moloney virus reverse transcriptase (21 U/µl, Boehringer) to the reaction solution, the resulting solution was maintained at 42° C. for 1 hour to allow synthesis of the cDNA. The same strategy was used to clone the sequence coding for the variable region of the light chain using VK₁FOR as the primer.

B) Amplification of the DNAs coding for the variable regions

For amplification of the sequence coding for the variable region of the heavy chain, 10 µl of the mixture obtained in A) were added to 50 pmoles of each of the primers (1 and 3), 250 µM of each of dATP, dTTP, dCTP and dGTP, 67 mM of Tris-HCl, 10 mM of MgCl₂, 17 mM of ammonium sulphate, 200 µg/ml of gelatine and 4 units of Taq polymerase (Boehringer) then made up to 100 µl with water. The reaction solution was covered with a layer of viscous paraffin (liquid) and subjected first to 3 amplification cycles with annealing at 45° C. and then to 30 cycles wherein each cycle comprised 1 minute of denaturation of the nucleic acids at 95° C., 1 minute of annealing of the primers at 50° C. and 2 minutes of elongation at 72° C.

After amplification the reaction solution was extracted twice with phenol-chloroform. The ds cDNA was then precipitated with ethanol and after separation by means of centrifugation was taken up in 100 µl of water and stored at 4° C.

The same procedure was used to amplify the sequence coding for the variable region of the light chain using as primers VK₁FOR and VK₁BACK.

The cDNAs coding for said variable regions were sequenced by the Sanger method (SEQUENASE kit version 2.0 a DNA sequencing but available from USB) and the nucleotide and amino acid sequences are reported in FIGS. 1 and 2.

EXAMPLE 3

Construction of recombinant vectors

The DNAs (10µl) derived from the amplification region were digested with the restriction enzyme pairs PstI and BstEII, and KpnI and BglII and the digestion products were subsequently fractionated on polyacrylamide gels (8%) by means of electrophoresis. Two bands were then eluted containing respectively a DNA fragment of about 309 bp comprising the gene VH5E8 delimited at the 5' end by a PstI site and at the 3' end by a BstEII site and a DNA fragment of 312 bases comprising the gene VK5E8 delimited at the 5' end by a KpnI site and at the 3' end by a BglII site. The DNA fragments were eluted from the gel and cloned at the PstI and BstEII, and KpnI and BglII sites of the vector pSMA-pSMD obtained in examples 1 and 2.

By means of transformation and selection techniques of the positive clones, the recombinant plasmids, namely pSM507, pSM438, pSM443 and pSM442 were isolated, with characteristics as reported in table 1.

EXAMPLE 4

Expression and Secretion of scFv in *B.subtilis*

Cells of *B.subtilis* SMS300 were made competent as follows: the overnight culture in VY medium (Veal Infusion Broth 25 g/l, Yeast Extract 5 g/l) was diluted 1:10 with minimum medium to which 5 mM MgSO$_4$, 0.5% glucose, 0.02% casamino acids and 50 µg/ml of essential amino acids (MMG1) were added, and grown for 4.5 hours at 37° C. and then further diluted 1:5 with minimum medium to which of 5 mM MgSO$_4$, 0.5% glucose, 5 µ/ml of essential amino acids and 0.01 of casamino acids (MMG2) were added.

Aliquots (1 ml) of said dilution were transformed with 1 µg of each recombinant vector and incubated at 37° C. for 90 minutes with vigorous agitation.

After selection of the transformants on VY medium plates containing chloramphenicol, the single colonies were inoculated into 100 ml flasks containing 10 ml of VY (DIFCO) with 5 µ/ml of chloramphenicol and grown overnight at 37° C.

Six ml of each culture were then centrifuged at 15,000 rpm for 2 minutes at 4° C. in order to separate the cellular pellet from the culture medium from which the exocellular proteins were isolated.

In practice, 40 µl of the culture were added to 10 µl of loading buffer of the following composition: 125 mM Tris-HCl pH6.8, 3% sodium dodecyl sulphate (SDS), 20% glycerol, 3% beta-mercaptoethanol and 0.025% bromophenol blue, then heat denatured (100° C.) and loaded onto polyacrylamide gel—SDS at 15%.

In parallel, the intracellular proteins were extracted after having resuspended the cellular pellet in 460 µl of 50 mM buffer containing 25% sucrose in TE pH 8.00. The mixture was incubated in the presence of 12 µof a 40 mg/ml lysozyme solution and 96 µl of EDTA 0.5M pH8, first at 37° C. for 30 minutes and then at 4° C. for 10 minutes. After adding 500 µl of 1% TRITON®, a polyethylene ether surfactant available from Sigma 50 mM of Tris-HCl pH 6.8 and 63 mM EDTA cell lysis was completed by sonication for 2 minutes in ice.

Centrifugation at 6,500 rpm for 10 minutes at 4° separated the supernatant (soluble fraction) from the pellet (insoluble fraction). The two protein fractions were made up to a volume of 1.2 ml with loading buffer and were boiled for 5 minutes to obtain denatured and reduced proteins. Subsequently 10 µl of each protein preparation were analysed on polyacrylamide gel (15%) under denaturing and reducing conditions.

After electrophoresis at 40 mA for about 3 hours, the protein bands on the two gels were observed by staining with Coomassie blue, transferred in parallel onto nitrocellulose filter (Schleicher and Schull 0.45 µm) and treated with rabbit serum producing anti-TAG antibodies and goat anti-rabbit IgG antibodies conjugated to peroxidase (Amersham). After staining with Coomassie blue, the following results were obtained:

TABLE 1

Production of scFv5E8 in *B. subtilis*

| plasmid | leader | promoter | total yield | soluble secretion |
|---------|--------|----------|-------------|-------------------|
| pSM507  | LS (I) | npr      | 30 mg/l     | 100%              |
| pSM438  | pelB   | npr      | 39 mg/l     | 25%               |
| pSM443  | LS (I) | Pc       | 10 mg/l     | 100%              |
| pSM442  | pelB   | Pc       | 200 mg/l    | 0                 |

EXAMPLE 5

Characterisation of the Antibody

The antibody ScFv5E8 was isolated from the culture medium of *B.subtilis* SMS300 (pSM507) cells by means of gel filtration on columns TSK125+TSK250 with a flow of 1 ml/minute, using PBS as eluent and an injection volume of 2 ml. Fractions were collected every 2 minutes at 2.0 ml/fraction and each fraction was injected onto BIACORE®, a surface plasmon resonance spectroscope available from Pharmacia Biosensor (Upsala, Sweden) to verify immunoreactivity with the antigen alpha hCG fixed to the sensor.

The results are reported in the following table.

TABLE 2

|       | scFv5E8              | MAb 5E8               |
|-------|----------------------|-----------------------|
| Kass  | $3.952 \times 10^5$  | $1.415 \times 10^5$   |
| Kdiss | $6.386 \times 10^{-4}$ | $2.300 \times 10^{-6}$ |
| KD    | $1.616 \times 10^{-9}$ | $1.696 \times 10^{-11}$ |
| KA    | $6.173 \times 10^8$  | $5.882 \times 10^{10}$ | where: Kass and Kdiss are the constants of kinetic association and dissociation; KD is the dissociation constant at equilibrium; KA is the affinity constant.

The results show that the association constant for scFv5E8 is similar to that of MAb 5E8 while the Kdiss is about 300 times greater than that of the monoclonal antibody of origin. These values are comparable with those obtained by Borrebaeck et al., (Biotech. 10:697–698, 1992) which compare a monoclonal antibody and its monofunctional derivative (Fab) prepared by means of proteolysis and indicate the maintenance of interaction characteristics at the binding site level of scFv produced in *B.subtilis* compared with the monoclonal antibody of origin.

---

We claim:

1. An expression and secretion recombinant vector of B.subtilis comprising:

1) the promoter of the gene coding for neutral protease in B.subtilis BGSC 1A341;

2) the secretion sequence (I) (SEQ ID NO:5)

5' ATG AGA AGC AAA AAA ACG CGT ATC AGC
   TTG TTG TTT GCG TTA ACG TTA ATC TTT
   ACG ATG GCA TTC AGC GGC CGC TCT GCC
   ATG GCC 3';

and 3) a DNA sequence coding for a molecule having the sequence VH-L-VK-(TAG)$_n$ or VK-L-VH-(TAG)$_n$ where VH and VK are the variable regions of the heavy and light chains of an antibody of interest; L is the peptide linker Val-Ser-Ser-(Gly$_4$-Ser)$_3$(SEQ ID NO:7); TAG is a peptide recognised by anti-peptide antibodies and n is 1 or 0.

2. The recombinant vector as defined in claim 1, wherein the peptide TAG has the amino acid sequence Met-Glu-Glu-Leu-Met-Ile-Glu-Gly-Arg (SEQ ID NO:3).

3. The recombinant vector as defined in claim 1, wherein VH and VK are the variable regions of the heavy and light chains of the monoclonal antibody MAb5E8 specific for sub-unit alpha of human chorionic gonadotropin.

4. The recombinant vector as defined in claim 1, filed as ATCC 69173.

5. The recombinant vector as defined in claim 1, obtained by:

(a) synthesizing an oligonucleotide comprising the secretion sequence (I), the sequence coding for the peptide linker and, optionally, the sequence coding for the peptide TAG, wherein said oligonucleotide contains unique restriction sites allowing the insertion of the sequence coding from the variable region of the heavy or light chain of the antibody downstream of the secretion sequence (I) and upstream of the peptide linker and the insertion of the sequence coding for the variable region of the light or heavy chain of the antibody downstream of the peptide linker and upstream of the peptide TAG;

(b) cloning said oligonucleotide in a plasmid vector SM308 ATCC 68047;

(c) cloning the DNA sequences coding for the variable region of the heavy and light chains of the antibody of interest in the restriction sites of the oligonucleotide; and (d) isolating the recombinant vector.

6. The recombinant vector as defined in claim 5, wherein the oligonucleotide of stage a) has the sequence (SEQ ID NO:8):

```
5' GAA TTC TTA TGA GAA GCA AAA AAA CGC GTA TCA
  GCT TGT TGT TTG CGT TAA CGT TAA TCT TTA CGA
  TGG CAT TCA GCG GCC GCT CTG CCA TGG CCG CAC
  AGG TCC AAC TGC AGC CTA TGG TCA CCG TCT CCT
  CAG GTG GCG GTG GCT CTG GCG GTG GTG GGT CGG
  GTG GCG GCG GAT CTG ACA TTC AAG GTA CCC CCT
  GAG ATC TCA TGG AAG AAC TTA TGA TCG AGG GTA
  GGT AAG TCG ACA AGC TT 3'.
```

7. The recombinant vector as defined in claim 5, wherein the DNA sequences of stage c) code for the variable regions of the heavy and light chain of the monoclonal antibody MAb 5E8 specific for sub-unit alpha of human chorionic gonadotropin.

8. A host microorganism transformed with a recombinant vector as defined in claim 1, wherein said microorganism is selected from the B.subtilis group.

9. The microorganism as defined in claim 6, which is B.subtilis SMS300 (pSM507) ATCC 69173.

10. A process for the exocellular preparation of a molecule having the sequence VH-L-VK-(TAG)$_n$ or VK-L-VH-(TAG)$_n$ where VH and VK are the variable regions of the heavy and light chains of an antibody of interest;

L is a peptide linker having the sequence Val-Ser-Ser (Gly$_4$-Ser)$_3$;

TAG is a peptide recognized by anti-peptide antibodies; and n is 1 or 0, comprising the steps of:

cultivating in a culture medium of strain of Bacillus subtilis transformed with a recombinant vector as defined in claim 1; and separating and purifying said molecule from said culture medium.

11. The process as defined in claim 10, wherein B.subtilis is B.subtilis SMS300 (pSM507) ATCC 69173 and the secreted antibody is scFv5E8 specific for sub-unit alpha of human chorionic gonadotropin.

12. A DNA molecule having the nucleotide sequence (SEQ ID NO:5)

```
5' ATG AGA AGC AAA AAA ACG CGT ATC AGC TTG
   TTG TTT GCG TTA ACG TTA ATC TTT ACG ATG
   GCA TTC AGC GGC CGC TCT GCC ATG GCC 3'
```

* * * * *

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
( A ) LENGTH: 339 base pairs
( B ) TYPE: nucleic acid
( C ) STRANDEDNESS: single
( D ) TOPOLOGY: linear ( i i ) MOLECULE TYPE: DNA (genomic)

(v) FRAGMENT TYPE: N-terminal (vi) ORIGINAL SOURCE:
    (G) CELL TYPE: Hybridoma
    (H) CELL LINE: 5E8

(ix) FEATURE:
    (A) NAME/KEY: CDS
    (B) LOCATION: 1..339

(xi) SEQUENCE DESCRIPTION: SEQ ID NO:1:

```
CAG GTC CAA CTG CAG CAG TCG GGG GCA GAG CTT ATG AAG CCA GGG GCC    48
Gln Val Gln Leu Gln Gln Ser Gly Ala Glu Leu Met Lys Pro Gly Ala
 1               5                  10                  15

TCA GTC AAG TTG ACA GCT TCC TGC TCT GGC TTC AGC ATT AAA GAC ACC    96
Ser Val Lys Leu Thr Ala Ser Cys Ser Gly Phe Ser Ile Lys Asp Thr
            20                  25                  30

TAT ATG CAC TGG GTG AAG CAG AGG CCT GAA CAG GGC CTG GAG TGG ATT   144
Tyr Met His Trp Val Lys Gln Arg Pro Glu Gln Gly Leu Glu Trp Ile
        35                  40                  45

GGA AGA ATT GAT CCT GCG AAT GGT AAT ACT AAA TAT GAC CCG AAG TTC   192
Gly Arg Ile Asp Pro Ala Asn Gly Asn Thr Lys Tyr Asp Pro Lys Phe
    50                  55                  60

CAG GGC AAG GCC ACT ATA ACA GCA GAC ACA TCC TCC AAC ACA GCC TAC   240
Gln Gly Lys Ala Thr Ile Thr Ala Asp Thr Ser Ser Asn Thr Ala Tyr
 65                 70                  75                  80

CTG CAG CTC AGC AGC CTG ACA TCT GAG GAC ACT GCC GTC TAT TAC TGC   288
Leu Gln Leu Ser Ser Leu Thr Ser Glu Asp Thr Ala Val Tyr Tyr Cys
                85                  90                  95

CAT AGG TTC GAA TTT GCT ATG GAC TAC TGG GGC CAA GGG ACC ACG GTC   336
His Arg Phe Glu Phe Ala Met Asp Tyr Trp Gly Gln Gly Thr Thr Val
            100                 105                 110

ACC                                                                339
Thr
```

(2) INFORMATION FOR SEQ ID NO:2:

(i) SEQUENCE CHARACTERISTICS:
        (A) LENGTH: 113 amino acids
        (B) TYPE: amino acid
        (D) TOPOLOGY: linear (ii) MOLECULE TYPE: protein (xi) SEQUENCE DESCRIPTION: SEQ ID NO:2:

```
Gln Val Gln Leu Gln Gln Ser Gly Ala Glu Leu Met Lys Pro Gly Ala
 1               5                  10                  15

Ser Val Lys Leu Thr Ala Ser Cys Ser Gly Phe Ser Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Lys Ala Thr Ile Thr Ala Asp Thr Ser Ser Asn Thr Ala Tyr
 65                 70                  75                  80

Leu Gln Leu Ser Ser Leu Thr Ser Glu Asp Thr Ala Val Tyr Tyr Cys
                85                  90                  95

His Arg Phe Glu Phe Ala Met Asp Tyr Trp Gly Gln Gly Thr Thr Val
            100                 105                 110

Thr
```

(2) INFORMATION FOR SEQ ID NO:3:

(i) SEQUENCE CHARACTERISTICS:
        (A) LENGTH: 333 base pairs
        (B) TYPE: nucleic acid
        (C) STRANDEDNESS: single
        (D) TOPOLOGY: linear (ii) MOLECULE TYPE: DNA (genomic)

(v) FRAGMENT TYPE: internal (vi) ORIGINAL SOURCE:
        (G) CELL TYPE: Hybridoma
        (H) CELL LINE: 5E8

(ix) FEATURE:
        (A) NAME/KEY: CDS
        (B) LOCATION: 1..333

(xi) SEQUENCE DESCRIPTION: SEQ ID NO:3:

```
GAC ATT CAA GGT ACC CAG TCT CCA GCT TCC TTA GTT GTA TCT CTG GGG    48
Asp Ile Gln Gly Thr Gln Ser Pro Ala Ser Leu Val Val Ser Leu Gly
 1               5                  10                  15

CAG AGG GCC ACC ATC TCA TGC AGG GCC AGC AAA AGT GTC AGT GCA TCT    96
Gln Arg Ala Thr Ile Ser Cys Arg Ala Ser Lys Ser Val Ser Ala Ser
                20                  25                  30

GGC TAT AGT TAT GTG AAT TGG TAT CAA CAG AAA CCA GGA CAG CCA CCC   144
Gly Tyr Ser Tyr Val Asn Trp Tyr Gln Gln Lys Pro Gly Gln Pro Pro
            35                  40                  45

AAA CTC CTC ATC TAT CTT GCA TCC AAC CTA GAA TCT GGG GTC CCT GCC   192
Lys Leu Leu Ile Tyr Leu Ala Ser Asn Leu Glu Ser Gly Val Pro Ala
        50                  55                  60

AGG TTC AGT GGC AGT GGG TCT GGG ACA GAC TTC ACC CTC AAC ATC CAT   240
Arg Phe Ser Gly Ser Gly Ser Gly Thr Asp Phe Thr Leu Asn Ile His
 65                 70                  75                  80

CCT GTG GAG GAG GAG GAT GCT GCA ACT TAT TAC TGT CAG CAC AGT AGG   288
Pro Val Glu Glu Glu Asp Ala Ala Thr Tyr Tyr Cys Gln His Ser Arg
                85                  90                  95

GAG CTT CCG CTC ACG TTC GGT GCT GGG ACC AAG CTG GAG ATC TCC       333
Glu Leu Pro Leu Thr Phe Gly Ala Gly Thr Lys Leu Glu Ile Ser
                100                 105                 110
```

(2) INFORMATION FOR SEQ ID NO:4:

(i) SEQUENCE CHARACTERISTICS:
        (A) LENGTH: 111 amino acids
        (B) TYPE: amino acid
        (D) TOPOLOGY: linear (ii) MOLECULE TYPE: protein (xi) SEQUENCE DESCRIPTION: SEQ ID NO:4:

```
Asp Ile Gln Gly Thr Gln Ser Pro Ala Ser Leu Val Val Ser Leu Gly
 1               5                  10                  15

Gln Arg Ala Thr Ile Ser Cys Arg Ala Ser Lys Ser Val Ser Ala Ser
                20                  25                  30

Gly Tyr Ser Tyr Val Asn Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
        50                  55                  60

Arg Phe Ser Gly Ser Gly Ser Gly Thr Asp Phe Thr Leu Asn Ile His
 65                 70                  75                  80

Pro Val Glu Glu Glu Asp Ala Ala Thr Tyr Tyr Cys Gln His Ser Arg
                85                  90                  95
```

Glu Leu Pro Leu Thr Phe Gly Ala Gly Thr Lys Leu Glu Ile Ser
             100                 105                 110

( 2 ) INFORMATION FOR SEQ ID NO:5:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: sig_peptide
        ( B ) LOCATION: 1..87

( i x ) FEATURE:
        ( A ) NAME/KEY: CDS
        ( B ) LOCATION: 1..87

( x i ) SEQUENCE DESCRIPTION: SEQ ID NO:5:

ATG AGA AGC AAA AAA ACG CGT ATC AGC TTG TTG TTT GCG TTA ACG TTA        48
Met Arg Ser Lys Lys Thr Arg Ile Ser Leu Leu Phe Ala Leu Thr Leu
 1               5                  10                  15

ATC TTT ACG ATG GCA TTC AGC GGC CGC TCT GCC ATG GCC                    87
Ile Phe Thr Met Ala Phe Ser Gly Arg Ser Ala Met Ala
             20                  25

( 2 ) INFORMATION FOR SEQ ID NO:6:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

Met Arg Ser Lys Lys Thr Arg Ile Ser Leu Leu Phe Ala Leu Thr Leu
 1               5                  10                  15

Ile Phe Thr Met Ala Phe Ser Gly Arg Ser Ala Met Ala
             20                  25

( 2 ) INFORMATION FOR SEQ ID NO:7:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:7:

Val Ser Ser Gly Gly Gly Gly Ser Gly Gly Gly Gly Ser Gly Gly Gly
 1               5                  10                  15

Gly Ser ( 2 ) INFORMATION FOR SEQ ID NO:8:

( i ) SEQUENCE CHARACTERISTICS:
        ( A ) LENGTH: 248 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
  ( A ) NAME/KEY: sig_peptide
  ( B ) LOCATION: 9..95

( i x ) FEATURE:
  ( A ) NAME/KEY: CDS
  ( B ) LOCATION: 9..95

( x i ) SEQUENCE DESCRIPTION: SEQ ID NO:8:

```
GAATTCTT ATG AGA AGC AAA AAA ACG CGT ATC AGC TTG TTG TTT GCG TTA          50
         Met Arg Ser Lys Lys Thr Arg Ile Ser Leu Leu Phe Ala Leu
          1           5                  10

ACG TTA ATC TTT ACG ATG GCA TTC AGC GGC CGC TCT GCC ATG GCC               95
Thr Leu Ile Phe Thr Met Ala Phe Ser Gly Arg Ser Ala Met Ala
 15              20                  25

GCACAGGTCC AACTGCAGCC TATGGTCACC GTCTCCTCAG GTGGCGGTGG CTCTGGCGGT         155

GGTGGGTCGG GTGGCGGCGG ATCTGACATT CAAGGTACCC CCTGAGATCT CATGGAAGAA        215

CTTATGATCG AGGGTAGGTA AGTCGACAAG CTT                                      248
```

( 2 ) INFORMATION FOR SEQ ID NO:9:

( i ) SEQUENCE CHARACTERISTICS:
    ( A ) LENGTH: 29 amino acids
    ( B ) TYPE: amino acid
    ( D ) TOPOLOGY: linear ( i i ) MOLECULE TYPE: protein ( x i ) SEQUENCE DESCRIPTION: SEQ ID NO:9:

```
Met Arg Ser Lys Lys Thr Arg Ile Ser Leu Leu Phe Ala Leu Thr Leu
 1           5                  10                  15

Ile Phe Thr Met Ala Phe Ser Gly Arg Ser Ala Met Ala
             20                  25
```

( 2 ) INFORMATION FOR SEQ ID NO:10:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( v ) FRAGMENT TYPE: C-terminal ( x i ) SEQUENCE DESCRIPTION: SEQ ID NO:10:

```
Met Glu Glu Leu Met Ile Glu Gly Arg
 1               5
```

( 2 ) INFORMATION FOR SEQ ID NO:11:

( i ) SEQUENCE CHARACTERISTICS:
    ( A ) LENGTH: 227 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: CDS
    ( B ) LOCATION: 9..74

( i x ) FEATURE:
    ( A ) NAME/KEY: sig_peptide
    ( B ) LOCATION: 9..74

( x i ) SEQUENCE DESCRIPTION: SEQ ID NO:11:

```
GAATTCAT ATG AAA TAC CTA TTG CCT ACG GCC GCC GCT GGA TTG TTA TTA          50
         Met Lys Tyr Leu Leu Pro Thr Ala Ala Ala Gly Leu Leu Leu
          1               5                   10

CTC GCT GCC CAA CCA GCC ATG GCC GCACAGGTCC AACTGCAGCC TATGGTCACC          104
Leu Ala Ala Gln Pro Ala Met Ala
 15                  20

GTCTCCTCAG GTGGCGGTGG CTCTGGCGGT GGTGGGTCGG GTGGCGGCGG ATCTGACATT        164

CAAGGTACCC CCTGAGATCT CATGGAAGAA CTTATGATCG AGGGTAGGTA AGTCGACAAG        224

CTT                                                                      227
```

( 2 ) INFORMATION FOR SEQ ID NO:12:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Met Lys Tyr Leu Leu Pro Thr Ala Ala Ala Gly Leu Leu Leu Leu Ala
 1               5                   10                  15
Ala Gln Pro Ala Met Ala
             20
```

( 2 ) INFORMATION FOR SEQ ID NO:13:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..34
        ( D ) OTHER INFORMATION: /note= "PRIMER"

( x i ) SEQUENCE DESCRIPTION: SEQ ID NO:13:

```
TGAGGAGACG GTGACCCTGG TCCCTTGGCC CCAG                                     34
```

( 2 ) INFORMATION FOR SEQ ID NO:14:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..22
        ( D ) OTHER INFORMATION: /note= "PRIMER"

( x i ) SEQUENCE DESCRIPTION: SEQ ID NO:14:

```
GTTAGATCTC CAGCTTGGTC CC                                                  22
```

( 2 ) INFORMATION FOR SEQ ID NO:15:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear -continued ( i i ) MOLECULE TYPE: DNA (genomic)

( i x ) FEATURE:
            ( A ) NAME/KEY: modified_base
            ( B ) LOCATION: 5..6
            ( D ) OTHER INFORMATION: /mod_base=i ( i x ) FEATURE:
            ( A ) NAME/KEY: modified_base
            ( B ) LOCATION: 8
            ( D ) OTHER INFORMATION: /mod_base=i ( i x ) FEATURE:
            ( A ) NAME/KEY: modified_base
            ( B ) LOCATION: 20
            ( D ) OTHER INFORMATION: /mod_base=i ( i x ) FEATURE:
            ( A ) NAME/KEY: misc_feature
            ( B ) LOCATION: 1..22
            ( D ) OTHER INFORMATION: /note= "PRIMER"

( x i ) SEQUENCE DESCRIPTION: SEQ ID NO:15:

AGGTNNANCT GCAGSAGTCN GG                                    22

( 2 ) INFORMATION FOR SEQ ID NO:16:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) MOLECULE TYPE: DNA (genomic)

( i x ) FEATURE:
            ( A ) NAME/KEY: misc_feature
            ( B ) LOCATION: 1..24
            ( D ) OTHER INFORMATION: /note= "PRIMER"

( x i ) SEQUENCE DESCRIPTION: SEQ ID NO:16:

GACATTCAGG GTACCAGTC TCCA                                   24